United States Patent

Sattizahn et al.

[11] Patent Number: 5,884,273
[45] Date of Patent: Mar. 16, 1999

[54] MICRO-COMPUTER AND PRINTER FOR PRINTING A PRESCRIPTION SLIP

[75] Inventors: Carmen M Sattizahn; Gregory A Neal, both of Charlotte, N.C.

[73] Assignee: Carmen M Neal, Charlotte, N.C.

[21] Appl. No.: 648,545

[22] Filed: May 16, 1996

[51] Int. Cl.⁶ ............................................. G06F 159/00
[52] U.S. Cl. ............................ 705/3; 395/203; 283/900
[58] Field of Search ........................ 705/2, 3; 364/146, 364/710.01, 710.02, 519; 283/900, 67; 395/202, 203, 924, 117; 101/93.04, 93.14; 282/3 R; 53/411; 346/76 PH; 235/380; 128/695 R; 434/109

[56] References Cited

U.S. PATENT DOCUMENTS

| | | | |
|---|---|---|---|
| 4,476,381 | 10/1984 | Rubin | 235/375 |
| 4,539,906 | 9/1985 | Ogura | 101/93.14 |
| 4,835,372 | 5/1989 | Gombrich et al. | 235/375 |
| 4,847,764 | 7/1989 | Halvorson | 364/413.02 |
| 4,850,009 | 7/1989 | Zook et al. | 379/96 |
| 4,853,521 | 8/1989 | Claeys et al. | 235/375 |
| 4,857,713 | 8/1989 | Brown | 235/375 |
| 4,875,174 | 10/1989 | Olodort et al. | 364/519 |
| 4,918,604 | 4/1990 | Baum | 364/413.01 |
| 4,932,682 | 6/1990 | Miller | 282/3 R |
| 4,972,657 | 11/1990 | McKee | 53/411 |
| 5,006,699 | 4/1991 | Felkner et al. | 235/472 |
| 5,028,934 | 7/1991 | Kasai et al. | 346/76 PH |
| 5,136,285 | 8/1992 | Okuyama | 340/870.11 |
| 5,153,585 | 10/1992 | Negishi et al. | 340/870.28 |
| 5,229,584 | 7/1993 | Erickson | 235/375 |
| 5,296,688 | 3/1994 | Hamilton et al. | 235/375 |
| 5,483,624 | 1/1996 | Christopher et al. | 395/117 |
| 5,528,021 | 6/1996 | Lassus et al. | 235/380 |
| 5,630,664 | 5/1997 | Farrelly | 128/695 R |
| 5,642,906 | 7/1997 | Foote et al. | 283/67 |
| 5,737,539 | 4/1998 | Edelson et al. | 395/203 |

OTHER PUBLICATIONS

"The Pepsi Challenge", by Laura Smith, PC Week, Sep. 18, 1995, v12, n37, pE1(2).

"For Oshawa General Hospital, IT is the best medicine", by Dale Burger, Computing Canada, Oct. 11, 1995, v21, n21, p1(2).

*Primary Examiner*—Kevin J. Teska
*Assistant Examiner*—Russell W. Frejd
*Attorney, Agent, or Firm*—Michael A. Mann; Nexsen Pruet Jacobs & Pollard LLP

[57] ABSTRACT

The present invention is a hand-held micro-computer with an attached printer that receives input from a physician and prints out a legible prescription slip for the physician's signature. The micro-computer has a keypad, display, and memory. The memory stores information about prescription drugs and physicians who have access to the micro-computer. When a physician wants to "write" or prepare a prescription slip, the physician enters a personal identification number, thus gaining access to the micro-computer. The physician then selects a drug to prescribe, either by entering a drug identification number or scrolling through a list of drug names. After the specific drug has been selected, the physician may change the default information for that drug or accept it. Once the information is correct, the physician prints out the prescription slip on the attached printer. The prescription slip contains all the relevant and necessary information for the patient and pharmacists and need only be signed by the physician before it can be filled.

18 Claims, 3 Drawing Sheets

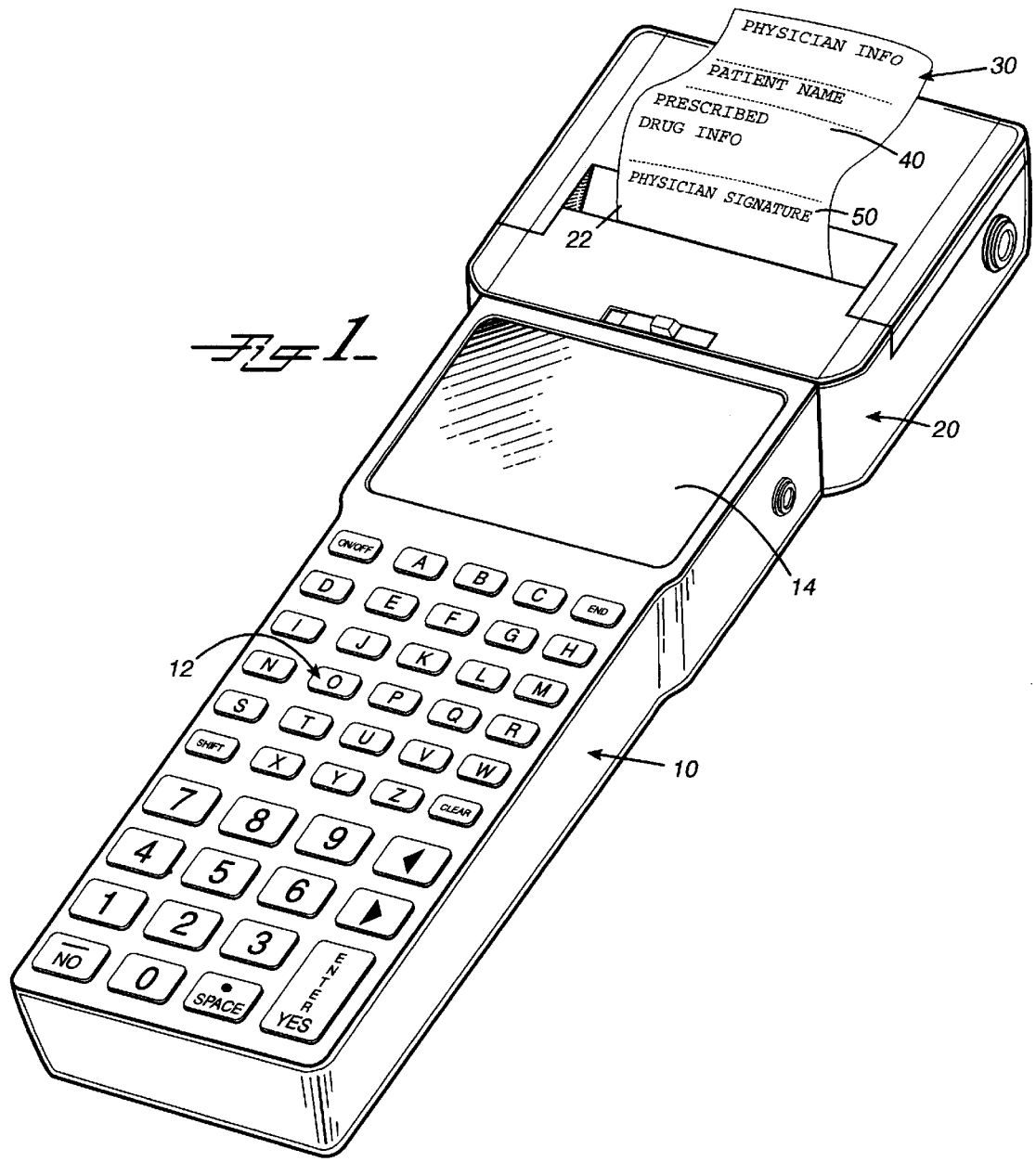

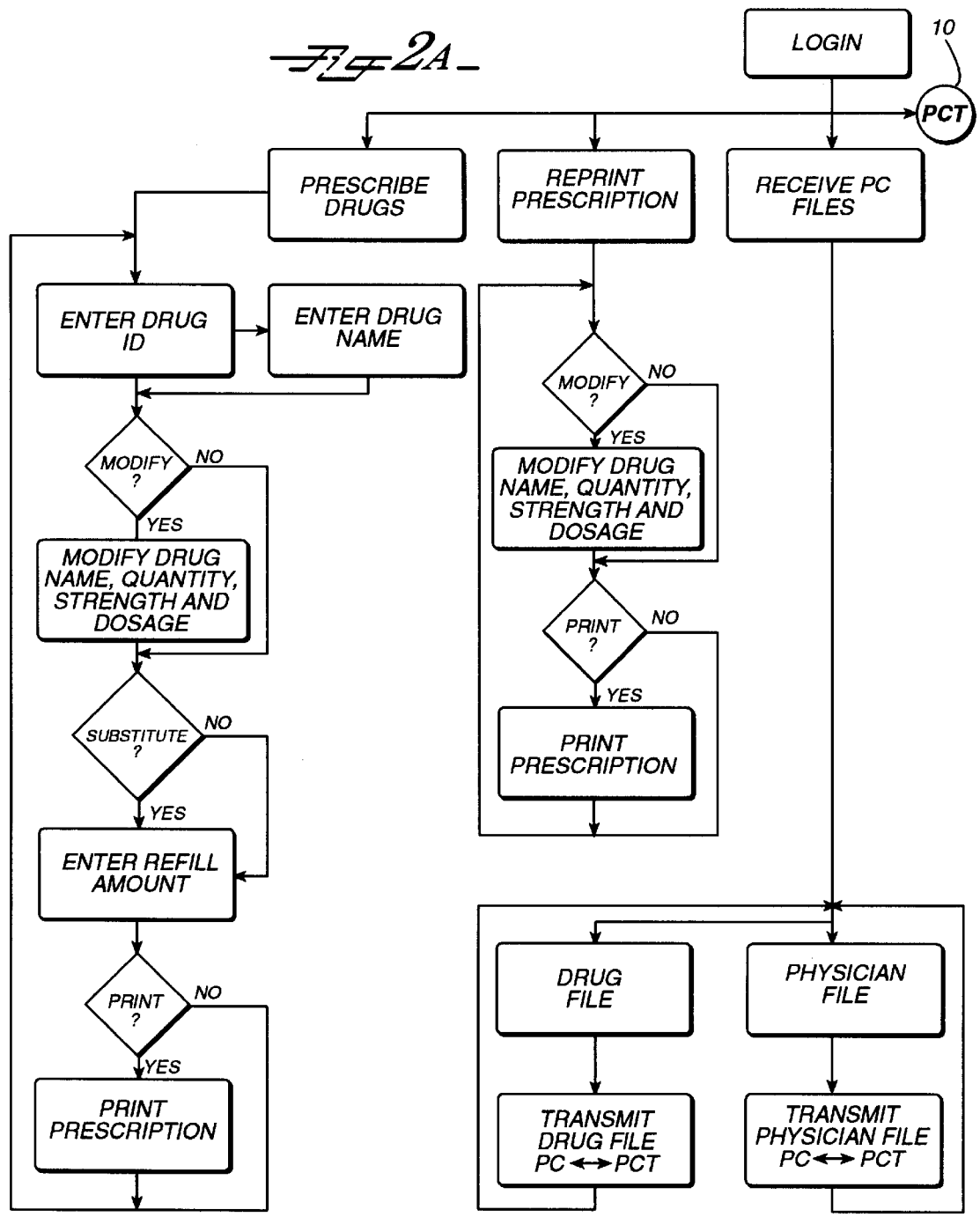

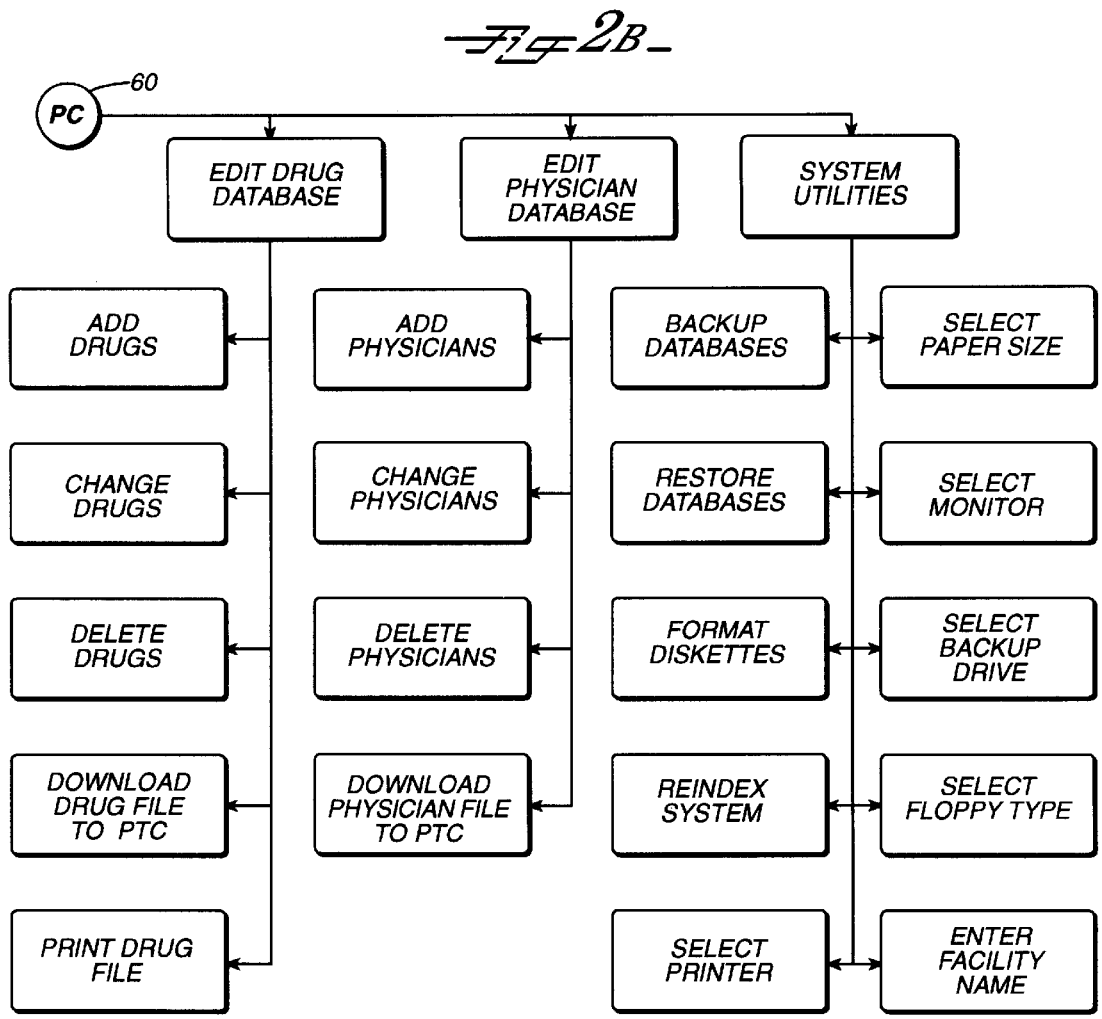
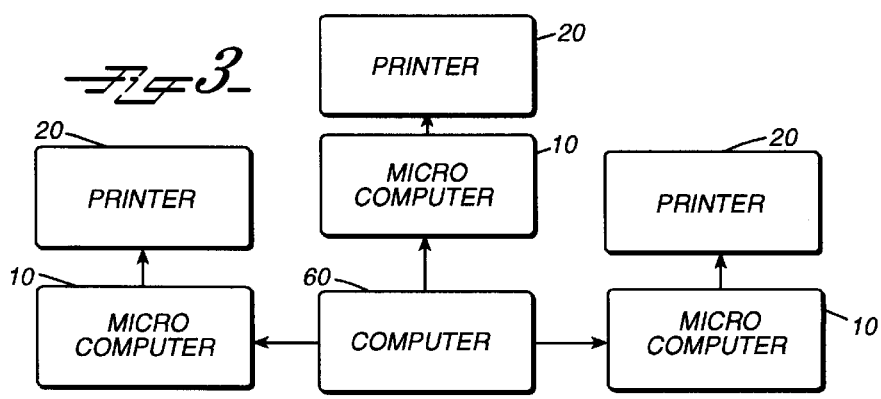

MICRO-COMPUTER AND PRINTER FOR PRINTING A PRESCRIPTION SLIP

BACKGROUND OF THE INVENTION

1. Field of the Invention

The present invention relates to a device for dispensing prescription slips. In particular, the present invention relates to a hand-held microcomputer and printer that will receive input and generate a prescription slip from a physician to a patient.

2. Discussion of Background

At times a physician's handwriting can be illegible, causing problems for medical personnel, pharmacists, and patients. In fact, the poor handwriting of physicians has become legendary. This problem arises when physicians make entries into the medical file of the patient, leave instructions for nurses, order procedures for patients, and prepare prescription slips for patients and pharmacists.

Several devices are available that alleviate the necessity of physicians writing the above information by hand. For example, physicians normally dictate information to be entered into the patient's file and instructions to nursing personnel, to reduce discrepancies between what is ordered and what is to be done. Additionally, word processors are sometimes used to enter information into patient files.

However, when physicians write prescriptions containing the name of a type of drug, amounts, and dosages, the writing can be illegible both to pharmacists and patients. If the pharmacist cannot read the prescription, the pharmacist may need to call the physician's office to clarify the handwriting. This not only delays filling the prescriptions, especially if they are being filled after office hours, but patients who urgently need medication are forced to wait unnecessarily. And from a physician's viewpoint, clarification takes time away from other office staff duties. If the pharmacist does not call the physician, other complications or errors may occur. In addition, many physicians abbreviate common drug names, which sometimes results in misinterpretations by pharmacists. These errors are common and have resulted in increased professional liability insurance premiums due to claims caused by prescription errors, which can and have resulted in disabilities and deaths. Consequently, it is imperative that a prescription slip be legibly written for the benefit of the pharmacist, who must read and dispense the appropriate medication, and for the benefit of the patient, who must read and take the appropriate amount of medication at the appropriate times.

Because physicians cannot be made or required to write more legibly, there is a need for a device that will legibly print out a prescription which includes the appropriate type of medication, quantities, and dosages.

SUMMARY OF THE INVENTION

According to its major aspects and broadly stated, the present invention is a hand-held micro-computer having a printer attached thereto that accepts input from a physician so that the input, combined with the medical information available in memory, prints a legible prescription slip. A prescription slip usually contains relevant information about the prescribed drug, including its strength, dosage, quantity, refill amount and whether a substitute is allowed. Additionally, the prescription slip will contain a line for the patient's name and the physician information including the physician's name, Drug Enforcement Agency (DEA) number, the physician's address, and a place for the physician to sign. It is also contemplated that the micro-computer can be used as a single unit with a main computer or as part of a larger group, where the group is supported by the main computer capable of storing all the information from each micro-computer.

The micro-computer is preferably a hand-held, portable computer having a display, a printer, and a keypad that permits alphanumeric input. The computer also has read-only-memory (ROM) and random access memory (RAM) that can be used by the user to store medical and drug information, and in an alternative embodiment, patient information. For instance, the computer can store information about different drugs, including usual dosages and a specific ID number associated with a certain drug. Additionally, in an alternative embodiment, the computer can contain important information about a specific patient, including known reactions for certain drugs and medication previously prescribed. Furthermore, the computer may be able to upload and download information about drugs, physicians and potentially patients from a main system, including the above information. Consequently, updated information on drugs, physicians, and patients may potentially be maintained in the portable units.

In use, it is contemplated that a physician will use the present invention to "write" a legible prescription slip for a patient. For this purpose the physician will log into the micro-computer, and then through a menu-driven program will enter the relevant information about the prescription. Once this information has been received and the microcomputer instructed to do so, the micro-computer will print out the prescription slip so that it may be signed by the physician.

The micro-computer's menu will also enable a physician to reprint a prescription slip, possibly with modified drug information, and to potentially upload or download information to and from the microcomputer and the main computer. Additionally, it will be possible to for the physician to edit the drug database and physician database so that new information about each may be changed, updated, or removed from the main system. Furthermore, the main computer and possibly the microcomputer will have a utilities function that will enable the user to configure the computer or micro-computer to the desired settings and to perform other necessary functions.

A major feature of the present invention is that the micro-computer prints out the prescription slip with all the relevant information. Therefore, other than the physician's signature and patient's name, all the information is in a typed format, thus legible to anyone who must read the slip. Consequently, the problem of not being able to read the physician's handwriting is alleviated.

Another feature of the present invention is the ability of the micro-computer to store information about the drugs and in an alternative embodiment information about patients. Having all the necessary information about the specific drugs in front of the physician, including usual dosages, strengths, and amounts, when the physician is writing the prescription, will help prevent mistakes, but will more importantly provide the physician with a plethora of information at his or her fingertips. Additionally, in an alternative embodiment, by having specific information on patient's readily available, physician's will be notified of potential allergic reactions of the patient before prescribing a certain drug. Consequently, the micro-computer will check for conflicts between the patient's record and the prescribed drug and notify the physician if any are present.

Still another feature of the present invention is the ability of the micro-computer to download and possibly upload information between a main computer. In this fashion a single or possibly several micro-computers can be used by a group of physicians, with each physician having the ability to use any one of the micro-computers. Furthermore, when it is necessary to update the relevant drug information carried by the micro-computers, this information can easily be downloaded to each unit.

Yet another feature of the present invention is the incorporation of a password or other ID number for each physician. This prevents someone other than the physician's from prescribing medication with the microcomputers.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective view of a micro-computer and printer according to a preferred embodiment of the present invention;

FIG. 2A is a schematic view of a flow chart for the micro-computer according to a preferred embodiment of the present invention;

FIG. 2B is a schematic view of a flow chart for the main computer according to a preferred embodiment of the present invention; and FIG. 3 is a schematic view of a flow chart according to an alternative embodiment of the present invention.

DETAILED DESCRIPTION OF A PREFERRED EMBODIMENT

Referring now to FIG. 1, a micro-computer 10 and a printer 20 for the preparation of a prescription slip 30 according to the preferred embodiment of the present invention is shown. Prescription slip 30 contains information about the prescribed drug and the physician who prescribed the drug. The physician information on prescription slip 30 may include the physician's name, address, phone number, personal identification number, Drug Enforcement Agency (DEA) number, and a place for the physician to sign. The drug information 40 contained on prescription slip 30 may include the prescribed drug's name, the strength, the quantity, the dosage, the refill amount, and whether a substitute is allowed. Additionally, prescription slip 30 will have a place for the patient's name and a place for the date or a printed date.

Micro-computer 10 is preferably a hand-held computer having both read-only-memory (ROM) and random-access-memory (RAM). The memory of micro-computer 10 is capable of storing a variety of information. In the preferred embodiment, the memory stores the drug information and the physician information. In an alternative embodiment, the memory may be able to store information on a variety of patients, including total or partial patient records or information on known drug allergies or other reactions.

Printer 20 is operatively connected to micro-computer 10 and will print prescription slip 30 upon demand by a user. Printer 20 can be connected to micro-computer 10 by a variety of methods known to those skilled in the art, including, but not limited to male-female electric plugs, cables, or by radio communication. In other words, it may be possible for printer 20 to be located apart from micro-computer 10 yet still be in operative communication. Printer 20 holds a roll of paper 22 and prints information on paper 22 to form prescription slip 30. The information that is printed by printer 20 is controlled by the user through micro-computer 10.

Those of ordinary skill in the art will recognize that a variety of hand-held micro-computers and printers may be used for the present system. The only requirement for micro-computer 10 is that it have the ability to store at least some drug information and be able to communicate to printer 20 so that prescription slip 30 can be printed.

In the preferred embodiment, micro-computer 10 and printer 20 are used with a main computer 60 which maintains the drug and physician databases. These databases, in whole or in part, may be downloaded to micro-computer 10, so that a prescription for a specific drug may be printed from micro-computer 10 or printer 20.

In another embodiment, micro-computer 10 and printer 20 are part of a larger system as shown in FIG. 3. This larger system comprises a main computer 60 and a number of micro-computers 10 and printers 20. Computer 60, as in the preferred embodiment, is capable of storing a relatively large amount of information as compared to micro-computer 10. For example, computer 60 may contain information on several thousands of prescription drugs, every patient of a specific physician group, or any other relevant information that would be kept in a physician practice group. Furthermore, computer 60 in the preferred embodiment is a personal computer or PC that is readily available in the marketplace and known to those of ordinary skill in the art.

Micro-computer 10 and computer 60 have means for transferring information between each other. This downloading or uploading process can be conducted over a physical cable connection or by remote communication such as radio waves. It should be noted that there are numerous methods and devices not listed above for uploading and downloading information between two computers. Being able to transfer information allows updated drug, physician, and/or possibly patient information to be transferred and stored within memory of micro-computer 10. It will be recognized that a variety of additional information can be uploaded or downloaded between micro-computer 10 and computer 60 without departing from the spirit and scope of the present invention.

In the use of micro-computer 10 and printer 20, it is contemplated that a physician will carry the device by hand to the patient's examining room, if the patient is visiting the physician's office. After diagnosing the patient's illness, the physician uses micro-computer 10 and printer 20 to prepare a prescription slip 30. Once prescription slip 30 has been prepared, the physician tears off prescription slip 30 from printer 20 and inserts the patient's name and then signs prescription slip 30 in the appropriate place.

In the preparation of prescription slip 30, as shown in FIGS. 2A, the physician first enters a personal identification number (PIN), thus activating micro-computer 10 and identifying the specific physician who is using the device. Additionally, after access has been obtained into micro-computer 10, a menu-driven system allows the physician to choose from a list of options. In order to "write" a prescription, the physician selects the appropriate selection and identifies the prescription drug by drug ID number or by scrolling through a list of drug names. Once the drug name has been selected, various default drug information is available, including the nominal quantities, strengths, and dosages for the specific drug. If the physician is satisfied with the default drug information, the physician can proceed to enter additional information, including whether substitutions are allowed and the number of refills available to the patient. After this additional information is entered, the physician can print out the prescription slip 30 for his or her signature, or can return to the beginning to start over the procedure. Additionally, in the alternative embodiment, microcomputer 10 would compare the prescribed drug with the patient's records to determine if there is a conflict. In other words if the patient has a known reaction to the specific drug, the physician will be notified by microcomputer 10.

If during the "writing" process, the physician wishes to change the default drug information, the physician will have that opportunity by selecting and entering the appropriate information through the menu-driven system on microcomputer 10. The information and selections can be entered and changed through the use of a keypad 12 and a display 14 on micro-computer 10. After the drug information has been modified as the physician wants it, the physician will enter information about a possible substitute and refill amount. Once the drug information has been entered and the physician approves, micro-computer 10 and printer 20 will print prescription slip 30 so that it may be signed by the physician. As with any other prescription slip, once the micro-computer generated slip is produced it can be taken by the patient to the pharmacist to be dispensed.

Other functions can also be performed on micro-computer 10 and printer 20 by the physician or other medical personnel. For example, as shown in FIG. 2A, the physician may reprint a prescription or modify a previous prescription and then reprint that one. Furthermore, as stated above, microcomputer 10 can receive and transmit information from and to computer 60, such as physician information and drug information. In FIG. 2A and 2B, computer 60 is referred to as PC and micro-computer 10 is referred to as PCT. The transfer of information is especially important when there are drug information updates and when a new physician will be using micro-computer 10 and printer 20.

Additionally, as shown in FIG. 2B, the users of computer 60 will be able to edit the drug database and a physician data base that is stored within computer 60. It is also possible to print the drug file and physician file stored within computer 60. The physician will also be able to perform other utility functions on computer 60. For instance, the physician will be able to backup databases, restore databases, format diskettes, re-index the system, select a printer type for computer 60, select a backup drive, and select a floppy disk type. Furthermore, under this heading the physician will be able to enter a facility name corresponding to the heading for prescription slip 30, showing the name, address, and phone number of the physician's practice. This will be downloaded to micro-computer 10 and printed on prescription slip 30. It will be recognized that computer 60 and micro-computer 10 can also be programmed to perform other relevant functions.

In the other embodiment, where micro-computer 10 and printer 20 are a part of a larger group with computer 60, those of ordinary skill in the art will recognize that a large variety of information can be stored and transferred by the use of micro-computer 10 and computer 60. For instance, it may be possible that prescription information can be uploaded from micro-computer 10 to a patient's record contained on computer 60. Additionally, it may also be possible to track the quantity of a specific prescribed drug and which physician prescribed it. Those skilled in the art will recognize the additional memory requirement for micro-computer 10 that will be necessary as the quantity and difficulty of the functions performed by micro-computer increase. Furthermore, because there are no prescription pads that can easily be stolen with no record or method of determining the theft, it would be easy to track and catch unauthorized prescription slips 30.

It will be apparent to those skilled in the art that many changes and substitutions can be made to the preferred embodiment herein described without departing from the spirit and scope of the present invention as defined by the appended claims.

What is claimed is:

1. A method of writing a prescription slip, said prescription slip having a drug name, quantity, strength, and dosage, said prescription slip being generated by a micro-computer and printer, said micro-computer having a keypad, a display, and a memory, said memory storing information on a plurality of drugs and physicians, said method comprising the steps of:

inputting a physician identification number corresponding to one of said plurality of physicians stored in said memory;

selecting an entry from a menu shown on said display of said micro-computer;

entering an identification corresponding to a drug, said drug having default characteristics, said default characteristics corresponding to said drug name, said quantity, said strength, and said dosage; and printing said prescription slip from said printer.

2. The method of writing a prescription slip as recited in claim 1, further comprising the step of modifying said default characteristics of said drug.

3. The method of writing a prescription slip as recited in claim 1, further comprising the step of choosing a refill amount for said drug, said refill amount appearing on said prescription slip after said prescription slip has been printed.

4. The method of writing a prescription slip as recited in claim 1, wherein said inputting step, said selecting step and said entering step are performed by depressing a series of keys on said keypad of said micro-computer.

5. The method of writing a prescription slip as recited in claim 1, further comprising the step of choosing whether to allow substitutions for said drug.

6. The method of writing a prescription slip as recited in claim 1, wherein said identification is a drug identification number.

7. The method of writing a prescription slip as recited in claim 1, wherein said identification is said drug name.

8. An apparatus for use in preparing a prescription slip, said apparatus comprising:

a micro-computer having
 memory means for storing information about prescription drugs, said information including names of said prescription drugs,
 selecting means for said user to select a prescription drug from said memory means; and a printer operatively connected to said micro-computer and responsive to said micro-computer so that said printer prints said prescription slip when said user selects said prescription drug from said memory, said prescription slip containing said name of said prescription drug wherein said apparatus will fit into the palm of the user.

9. The apparatus as recited in claim 8, wherein said information contains nominal dosages and strengths for said prescription drugs.

10. The apparatus as recited in claim 8, wherein said information contains nominal dosages and strengths for said prescription drugs, and wherein said printer prints said dosage and strength of said prescription drug on said prescription slip.

11. The apparatus as recited in claim 8, wherein said information contains nominal dosages and strengths for said prescription drugs, and wherein said selecting means allows the user to change said dosage and said strength of said prescription drug.

12. The apparatus as recited in claim 8, wherein said user selects said prescription drug by inputting a drug identification number.

13. The apparatus as recited in claim 8, wherein said user selects said prescription drug by selecting said name of said prescription drug from a list of said prescription drugs in said memory means.

14. The apparatus as recited in claim 8, wherein said micro-computer further comprises means for updating said information about said prescription drugs.

15. A system for generating a prescription slip, said system comprising:

a computer;

at least one micro-computer having communication means for communicating with said computer, said micro-computer having memory means for storing information about prescription drugs, said information including names of said prescription drugs, selecting means for said user to select a prescription drug from said memory means; and a printer operatively connected to said micro-computer and responsive to said micro-computer so that said printer prints said prescription slip when said user selects said prescription drug from said memory, said prescription slip containing said name of said prescription drug.

16. The system as recited in claim 15, wherein said communication means enables said information about said prescription drugs and information about physician's to be transferred between said computer and said micro-computer.

17. The system as recited in claim 15, wherein said information includes nominal dosages and strengths for said prescription drugs, and wherein said selecting means allows the user to change said dosage and said strength of said prescription drug.

18. The system as recited in claim 15, wherein said printer prints a dosage and strength for said prescription drug, a quantity, and refill amount for said prescription drug, a Drug Enforcement Agency number for a physician, and a location for a physician's signature and patient's name on said prescription slip.

* * * * *